United States Patent [19]

Bernatowicz

[11] Patent Number: 5,187,270
[45] Date of Patent: Feb. 16, 1993

[54] RACEMIZATION FREE ATTACHMENT OF AMINO ACIDS TO A SOLID PHASE

[75] Inventor: Michael S. Bernatowicz, Cambridge, Mass.

[73] Assignee: Millipore Corporation, Bedford, Mass.

[21] Appl. No.: 295,048

[22] Filed: Jan. 6, 1989

Related U.S. Application Data

[63] Continuation-in-part of Ser. No. 290,433, Dec. 27, 1988, abandoned.

[51] Int. Cl.$^5$ ............... C07D 233/64; C07C 261/00
[52] U.S. Cl. .................. 548/338.1; 548/496; 548/535; 548/311.4; 560/24; 560/27; 560/29; 560/30; 560/31; 560/32; 560/33; 562/575; 562/560; 562/561; 562/573; 562/571; 562/557; 562/563; 562/559; 562/445; 562/567
[58] Field of Search ............... 530/334, 335; 560/32, 560/24, 27; 558/271; 210/112.5; 548/344, 496, 535; 562/557, 445

[56] References Cited

PUBLICATIONS

Albericio et al. Int'l J. Peptide Prot. Res. vol. 26 (1985) pp. 92–97.
Bernatowicz, M. S. et al., *Tetrahedron Letters*, 30:4341–4344 (1989).
Merrifield, R. B., *J. Am. Chem. Soc.*, 85:2149–2154 (1963).
Atherton, E. et al., *J. C. S. Chem. Commun.*, 336–337 (1981).
Sieber, P. *Tet. Lett.*, 28:6147–6150 (1987).
Kirstgen, R. et al., *J. Chem. Soc., Chem. Commun.*, 1870–1871 (1987).
Mitchell, A. R. et al., *J. Org. Chem.*, 43:2845–2852 (1978).
Wang, S. S. et al., *J. Org. Chem.*, 42:1286–1290 (1977).
Colombo, R. et al., *Int. J. Peptide Protein Res.*, 21:118–126 (1983).
Dhaon, M. K. et al., *J. Org. Chem.*, 47:1962–1965 (1981).
Sheppard, R. C. and B. J. Williams, *Int. J. Peptide Protein Res.*, 20:451–454 (1982).
Matsueda, G. R. and E. Haber, *Anal. Biochem.*, 104:215–227 (1980).
Atherton, E. et al., *J. Chem. Soc., Perkin Trans I*, 538–546 (1981).
Mitchell, A. R. et al., *J. Am. Chem. Soc.*, 98:7357–7362 (1976).
Tam, J. P. et al., *Synthesis*, 955–957 (1979).
Tjoeng, F. S. and G. A. Heavner, *Synthesis*, 897–899 (1981).
Plaue, S. and D. Heissler, *Tetrahedron Letters*, 28:1401–1404 (1987).
Gisin, B. F., *Helevetica Chemica Acta*, 56:1476–1482 (1973).
Horiki, K. et al., *Chem. Letters*, 165–168 (1978).
Milligen Technical Bulletin for Pepsyn KA TM.
Arshady, R. et al., *J. Chem. Soc. Perkin Trans 1*, 529–537 (1981).
Atherton, E. et al., *J. C. S. Chem. Comm.*, 1151 (1981).
*MilliGen PepSynthesizer* TM *Model 9050 Operation Manual*, Chapter 3.

*Primary Examiner*—Merrell C. Cashion, Jr.
*Assistant Examiner*—Bennett Celsa
*Attorney, Agent, or Firm*—Hamilton, Brook, Smith & Reynolds

[57] ABSTRACT

This invention pertains to amino acids attached to a solid support in a racemization free manner and to a method of covalently linking amino acids to solid supports for use in solid phase peptide syntheses.

7 Claims, 5 Drawing Sheets

RACEMIZATION FREE ATTACHMENT OF AMINO ACIDS TO A SOLID PHASE

RELATED APPLICATION

This application is a continuation-in-part of U.S. Ser. No. 07/290,433, filed Dec. 27, 1988, now abandoned.

BACKGROUND OF THE INVENTION

A peptide is a natural or synthetic substance characterized by a specific sequence of component amino acids which are chemically linked together by amide bonds. A widely used approach to the chemical synthesis of peptides is known as the solid-phase method. (See Barany et al., *Int. J. Peptide Protein Res.* 30:705–39 [1987].) The feasibility of solid-phase synthesis was first demonstrated using an amino acid protected with carbobenzyloxy (Cbz) which was immobilized on a polystyrene compound via a benzyl ester linkage. (Merrifield, R. B., *J. Am. Chem. Soc.* 85:2149–54 [1963].) Since then, Merrifield has also used t-butyloxy-carbonyl (Boc) for $N\alpha$ protection.

A critical step in the synthesis of peptides by the solid-phase method is the covalent attachment, or "anchoring", of the first (C-terminal) amino acid to the solid support in a specific and controlled manner. When the urethane protecting group-based synthesis schemes were employed for solid-phase peptide synthesis, there were specific problems with the carboxyl group activation methods for anchoring the C-terminal amino acid (Atherton, E. et al., *J.C.S. Chem. Commun.* 336–7, [1981]; Sieber, P. *Tet. Lett.* 28, 6147–50 [1987]; Albericio, F. and Barany, G. *Int. J. Peptide Protein Res.* 26, 92–7 [1985]). These methods specifically suffer from low functionalization and/or partial racemization. Although solutions to such problems have been proposed (Sieber, P. *Tet. Lett.* 28:6147–50 [1987]; Albericio, F. and Barany. G., *Int. J. Peptide Protein Res.* 26:92–7 [1985]; Kirstgen, R. et al., *J. Chem. Soc., Chem. Commun.*, 1870-1 [1987]), none of these are entirely satisfactory for industrial scale production of amino acids anchored to solid supports.

Drawbacks of these solid phase methods using carboxyl group activation include the unavailability or expense of, and/or instability of the reagents required for carboxyl group activation. In addition, esterification via carboxyl group activation in some of these cases appears to require long reaction times for optimum yields. Finally, the ability to generalize these methods to all of the amino acids of common interest has not yet been demonstrated.

9-fluorenyl methyloxy carbonyl (Fmoc) protected amino acids have been used to prepare solid-phase bound amino acids. Racemization of the amino acid from one to about twenty percent has been observed by the currently used method for attachment of $N\alpha$-Fmoc amino acids to solid supports (Atherton E. et al., *J.C.S. Chem. Commun.* 336–337 [1981]). In another approach, amino acids are esterified directly to alkyl halides or polymeric alkyl halides without racemization. These methods require the laborious and expensive preparation of protected amino acid cesium salts. For Fmoc-amino acid cesium salts, the method (Columbo) has not been generally demonstrated, presumably due to poor solubility of some of these derivatives (e.g., Mitchell, A. R. et al., *J. Org. Chem.* 43:2845–52 [1978]; Wang, S. S. et al., *J. Org. Chem.* 42:1286–90 [1977]; Columbo, R., et al., *Int. J. Peptide Protein Res.* 21:118–26 [1983]). Alternate methods for production of solid support derivatives which utilize benzyl ester formation via reaction of activated carboxyl groups with benzyl alcohol derivatives in the presence of acylation catalyst have been shown to produce measurable amounts of racemization of the protected amino acid (Dhaon, M. K. et al., *J. Org. Chem.* 47:1962–1965 [1981]; Atherton, E. et al., *J.C.S. Chem. Commun.* 336–337 [1981]).

There exists a need for a general and inexpensive means for controlled and efficient anchoring of C-terminal amino acids to solid supports without significant racemization of the amino acids.

SUMMARY OF THE INVENTION

This invention pertains to amino acids attached to a solid phase in a racemization free manner and to a method of covalently linking amino acids to solid supports for use in solid phase peptide syntheses. This invention also pertains to new compounds which are used to covalently and specifically link amino acids to solid supports. This invention further pertains to a method of synthesizing peptides from the solid-support bound amino acid derivatives produced by the methods of this invention.

According to the method of this invention, a protected amino acid covalently bound to a solid support can be prepared having the general formula (I):

Z is an $N\alpha$ protecting group. B is one or more amino acids having protected or unprotected side chains. $R_1$ and $R_2$ are the same or different and are selected from the group consisting of hydrogen, linear or branched, saturated or unsaturated alkyl, aryl and benzyl. A is a substituted or unsubstituted aromatic ring. Y is a hydrocarbon chain having a linear or branched, saturated or unsaturated alkyl, aryl or aralkyl group and may be linked to A through an ether linkage. D is an oxygen or —NH— which may be linked to a spacer selected from the group consisting of one or more natural and unnatural amino acids or hydrocarbon chain having linear or branched saturated or unsaturated alkyl, aryl or aralkyl groups, the spacer being linked to the carbonyl through an oxygen or —NH— linkage. SS is a solid support which is bound to the carbonyl group through D.

The solid support bound compounds of this invention are used to synthesize specific peptide sequences using standard chemical protocols for the stepwise construction of peptides.

DETAILED DESCRIPTION OF THE INVENTION

This invention pertains to protected amino acid covalently linked to a solid support having the general formula (I):

Z is an $N\alpha$ protecting group. B is one or more amino acids having protected or unprotected side chains. Preferably, B is one amino acid. $R_1$ and $R_2$ are the same or different and are selected from the group consisting of hydrogen, linear or branched, saturated or unsaturated alkyl aryl and benzyl. Preferably, $R_1$ and $R_2$ are both hydrogen. A is a substituted or unsubstituted aromatic ring. Preferably the aromatic ring is a substituted or unsubstituted benzene ring wherein the benzene group is linked to C and Y at its para positions and where the substituents are selected from the group consisting of aryl, alkyl, halo, nitro alkoxy and combination thereof. Y is a hydrocarbon chain having a linear or branched, saturated or unsaturated alkyl, aryl or aralkyl group and may be linked to A through an ether linkage. Preferably Y is $-(O)_m-(CH_2)_n$ where m is one or zero and n is an integer from zero to twelve. D is a functional group on the solid support allowing the support to bind to the carbonyl. Preferably D is an oxygen or —NH— which may be linked to a spacer selected from the group consisting of one or more natural and unnatural amino acids or hydrocarbon chain having linear or branched, saturated or unsaturated alkyl, aryl or aralkyl groups, the spacer being linked to the carbonyl through an oxygen or —NH— linkage. SS is a solid support which is bound to the carbonyl group through functional group D. Preferable solid supports are Pepsyn TM, Pepsyn K TM and polystyrene resins.

The method of the present invention provides an economical means for producing derivatized solid supports which can be used in solid phase peptide synthesis. The method makes use of starting materials which are inexpensive and react at rapid reaction rates. Further, the present invention eliminates the need to use cesium salts of the $N\alpha$ protected amino acids such as Boc-amino acid—O—Cs$^+$ as used in the Mitchell method, or expensive and toxic additives such as 18-crown-6 as used in the Columbo method.

The method of the present invention provides a means for practical, controlled and efficient anchoring of C-terminal amino acids to solid supports without incurring racemization of the amino acids. Thus, peptides produced using the solid phase-bound amino acids of the present invention are produced in better yield and purity than peptides produced using conventional solid phase supports.

The above compound can be synthesized by two schemes detailed below. The intermediates of these syntheses are also novel compounds. A more detailed description of the reactants suitable for these syntheses follows below.

Scheme I

In a first scheme, carboxylic acid (II) with leaving group X undergoes a condensation reaction with an alcohol, phenol, thiol, thiophenol or heterocyclic equivalent in the presence of a condensing agent to yield the compound (III).

A, $R_1$, $R_2$ and Y are as defined above. X is a leaving group which can be readily displaced by a carboxylate in a subsequent synthetic step. A leaving group as defined herein is any electron withdrawing substituent which renders the carbon atom to which it is attached electrophilic thereby facilitating nucleophilic substitution reactions at that carbon. Preferable leaving groups are any halogen but may also be a sulfonyl group such as methane sulfonyl trifluoro methyl sulfonyl or p-toluene sulfonyl. In a preferred embodiment, compound (II) is 4-bromomethylphenoxyacetic acid or 4-iodomethylphenoxyacetic acid. W is either a sulfur atom or an oxygen atom. $R_3$ represents a group analogous to the alcohol, phenol, thiol, thiophenol, or heterocyclic equivalent of choice. Any alcohol, phenol, thiol, thiophenol, or heterocyclic equivalent can be used as a reagent so long as $R_3$ acts as a carboxyl protecting group. $R_3$ may or may not activate the carboxyl group to nucleophilic attack. If $R_3$ is such an activating group, it must produce compound (III) of sufficient stability such that $R_3$ is not transferred to the carboxyl group of the amino acid used in the subsequent synthetic step, yet it must be sufficiently reactive to render compound (IV) susceptible to nucleophilic displacement by atom D attached to a solid support to yield the compound of Formula I. Where $R_3$ is not a carbonyl activating group, it must be capable of removal under conditions which do not affect the $N\alpha$ and side chain protecting groups.

An $N\alpha$ protected amino acid is then esterified directly to the substituted aromatic ester (III) to yield the compound of the following formula:

wherein $R_1$, $R_2$, Y, A, W and $R_3$ have been previously defined. B represents an amino acid or peptide linked through its carboxyl group to the benzylic carbon of the compound. The amino acid can be a naturally occurring amino acid or modified versions thereof. Although B is shown as a single amino acid, it should be understood that B can represent more than one amino acid. The amino acid side chain may be optionally or necessarily protected with a side chain protecting group. Z is an $N\alpha$ protecting group. The term $N\alpha$ protecting group is intended to mean a structure that can bind to the amino acid through the $\alpha$-nitrogen atom and thus render the amino group unreactive. The $N\alpha$ protecting group should also be capable of being removed without destroying any peptide linkage produced by the methods of this invention. Preferably, Z is a base labile protecting group such as 9-fluorenylmethyloxycarbonyl protecting group (Fmoc).

In the esterification step, $N\alpha$ protected amino acid carboxylate anions are generated in solution and, as such, act as a nucleophile. An ester bond is then formed with the benzylic carbon of the substituted aromatic ester (III) by nucleophilic attack of amino acid carboxylates.

In the final step of the synthesis, the $N\alpha$ protected amino acid ester (IV) is coupled directly to a solid support using a catalyst to yield the compound of formula (I) as previously described.

In a preferred embodiment, a halogenated or sulfonated carboxylic acid (V) undergoes a condensation reaction with 2,4-dichlorophenol in the presence of a condensing agent to yield the compound (VI):

m is zero or one and n is an integer from zero to twelve. The compound of (VI) is then esterified to an $N\alpha$ protected amino acid to yield the compound of the following formula:

wherein Z, B, m and n have been previously defined. The compound (VII) is then coupled directly to a solid support to yield the compound of the formula:

wherein the variables have been defined previously.

Figure 1:
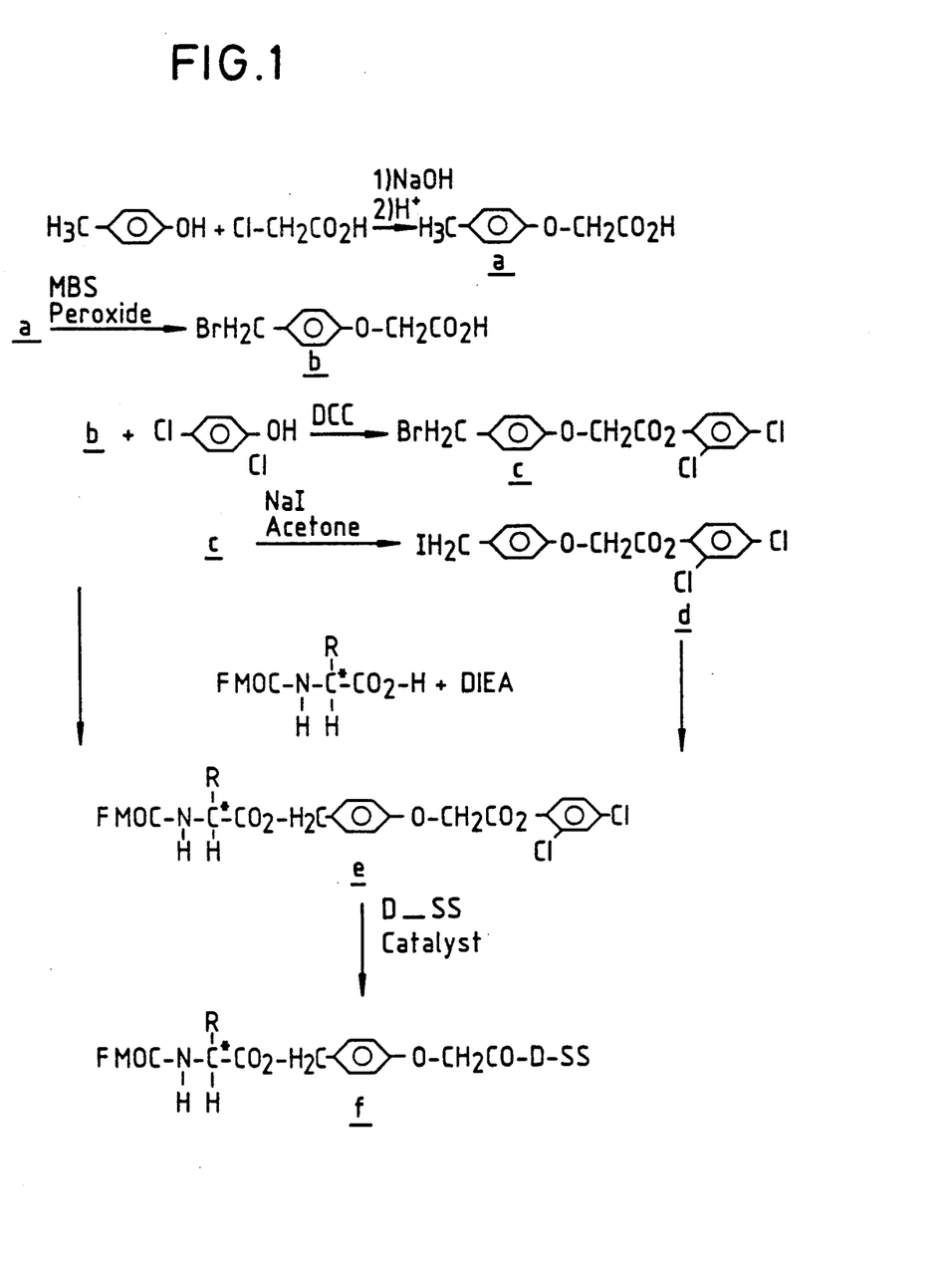
FIG. 1 is a schematic representation for racemization free attachment of C-terminal amino acids to solid supports for peptide synthesis.

The substituted aromatic carboxylic acid, 4-methylphenoxyacetic acid is used as a starting reactant; however, other substituted aromatic carboxylic acids may be used. The abbreviations used in FIG. 1 are explained as they are referred to in the following text which describes the process.

In the first step, 4-methylphenoxyacetic acid (a) is prepared by alkylation of p-cresol with chloroacetic acid in the presence of a suitable base, such as sodium hydroxide. Other isomers of 4-methylphenoxyacetic acid may be obtained using o-cresol or m-cresol. Alternate alkylating agents such as iodoacetic acid, bromoacetic acid or the equivalent thereof may be used. The reaction may be carried out in aqueous or suitable organic solvent or mixtures thereof and other bases such as potassium or lithium hydroxide, potassium carbonate, cesium carbonate, sodium hydroxide, sodium hydride, potassium hydride, or the equivalent thereof may be used to form the cresolate anion required for reaction. Acidification of the reaction mixture for product isolation is accomplished with aqueous hydrochloric acid, sulfuric acid, potassium hydrogensulfate or an equivalent proton source thereof.

In the subsequent synthetic step, 4-methylphenoxyacetic acid (a) is brominated by N-bromosuccinimide (NBS) to form 4-bromomethyl-phenoxyacetic acid (b) using chloroform or carbon tetrachloride as a solvent. The reaction is carried out in refluxing solvent in the presence of a free-radical initiator such as benzoyl peroxide or an equivalent thereof. Alternatively, the reaction may be carried out using other brominating agents such as N-bromoacetamide or equivalents thereof and may be initiated by light. Similarly, alkanes bromoform, carbon tetrabromide or an equivalent thereof may be used as solvent.

A suitable active ester of 4-bromomethylphenoxyacetic acid (b) is formed in the following synthetic step. This step is accomplished by condensation of b with 2,4-dichlorophenol using dicyclohexylcarbodiimide (DCC), as condensing agent. The reaction may be carried out in a variety of organic solvents such as ethyl acetate, methylene chloride, chloroform, dioxane, tetrahydrofuran, dimethylformide or an equivalent thereof. Other substituted phenols such as pentafluoro pentachloro, 2-nitro, 2,4-dinitro, 4-nitro, 2-chloro, 4-chloro, 2,4,5-trichloro, 2-bromo, 4-bromo, isomers of these or their equivalents may be used to provide active ester derivatives analogous to 2,4-dichlorophenyl-4-bromomethyl phenoxy acetate (c). Other analogous esters may be obtained by substituting appropriately structured alcohols, such as trichloroethanol, phenacyl alcohol, N-hydroxy compounds such as N-hydroxysuccinimide, hydroxyl substituted heterocycles, or their equivalents, for 2,4-dichlorophenol in this reaction. In addition, thioester analogs of (c) may be obtained by condensation of b with appropriately substituted thiols. For the conversion of b to c, or b to the above-stated analogs of c, alternative condensing agents or condensation chemistries may be employed. For example, other carbodiimides such as diisopropylcarbodiimide or its equivalent may be used. Similarly, carboxyl activation of b may be accomplished by conversion of b to its acid chloride via thionyl chloride or its equivalent, or conversion to a mixed anhydride via isobutylchloroformate, pivaloyl chloride, or their equivalents. Other known methods of carboxyl group activation may be employed.

In some instances the conversion of c to its iodide derivative, 2,4-dichlorophenyl-4-iodomethyl phenoxy acetate (d) may be advantageous before performing the subsequent chemical reactions depicted in FIG. 1. The halogen exchange reaction is carried out by addition of saturated anhydrous sodium iodide in acetone to the bromomethyl-active ester (c). For this reaction, potassium iodide, or an equivalent iodide may be substituted for sodium iodide and tetrahydrofuran or an equivalent may be substituted for acetone as solvent.

In the next step of the synthetic scheme, either the bromide (c) or iodide (d) derivative is used to alkylate Fmoc-amino acid carboxylate anions which are generated in solution by neutralization with a tertiary amine base such as diisopropylethylamine (DIEA). Fmoc refers to the 9-fluorenyl methyloxycarbonyl protecting group and R refers to the structure of the amino acid side chain and is dependent on the particular amino acid selected. For example, when $R=CH_3$, the amino acid is alanine (Ala), when $R=CH(CH_3)_2$, the amino acid is valine (Val), etc. The R, amino acid side chain, may include the structure of a protecting group, where necessary. The asterisk at the $\alpha$-carbon is used to designate this atom as a chiral center. Thus, D or L enantiomers of each amino acid may be used for this reaction. The stereochemistry is completely retained during the conversion of halides c or d to the product, $N\alpha$-9-fluorenylmethyloxycarbonylaminoacyl 4-oxymethylphenoxyacetic acid-2,4-dichlorophenylester (e). Thus, when optically pure. Fmoc-protected L-amino acids are used in the esterification, the products (e) obtained are of the L configuration and are uncontaminated with D isomer.

The esterification may be carried out in a variety of solvent or solvent mixtures including dimethylacetamide, dimethylformamide, N-methylpyrolidone, acetone and equivalents thereof. Alternate bases or hydrogen-bonding chemicals may be used to generate an effective protected amino acid carboxylate. These include triethylamine, tributylamine, cesium or potassium carbonate or bicarbonate, N-methylmorpholine, potassium fluoride, or equivalents thereof. Preferably, Fmoc is used as the $N\alpha$-protecting group; however, other protecting groups may be used for peptide synthesis such as t-butyloxycarbonyl (Boc), Dithiosuccinyl (Dts), carbobenzyloxycarbonyl (Cbz), 2-nitropyridinesulfenyl (Npys), trifluoroacetyl, 2(p-biphenylisopropyloxycarbonyl (Bpoc), 4-methoxybenzyloxycarbonyl (Pmz), tosyl, trityl, methoxy-substituted trityls, 9-phenylfluorenyl, 2-nitrophenylsulfenyl (Nps), benzyl, p-nitrocarbobenzyloxycarbonyl (p-$NO_2$Cbz), t-amyloxycarbonyl (Aoc), 2-(3,5-Dimethyloxyphenyl)-propyl-(2)-oxycarbonyl (Ddz), 2,2-[bis(4-nitrophenyl)]-ethyloxycarbonyl (Bnpeoc), adamantyloxycarbonyl (Adoc), 2,2,2-trichloroethyloxycarbonyl (Troc), and variously substituted analogs and isomers and their equivalents thereof.

Table 1 lists various carboxy-functionalized $N\alpha$-Fmoc protected amino acids (e) that have been prepared via iodide (d) or bromide (c) derivatives and the appropriate $N\alpha$-Fmoc-amino acids as indicated in FIG. 1. Proton NMR spectra of all the derivatives listed in Table 1 were consistent with the expected structures. The process is compatible with a complete range of side chain protecting groups useful in peptide synthesis. In addition to the side chain protecting groups indicated in Table 1 (for abbreviations, see Table 1 footnote), the process may be used with other side chain protecting groups, such as Cbz, various chloro, bromo, and methyl substituted Cbz groups, Pmz, p—$NO_2$Cbz, Aoc, Adoc, Bpoc, trifluoroacetyl, Nps, Npys, tosyl, variously substituted tosyls, Dts, Ddz, Bnpeoc, benzyl and various chloro, bromo, nitro, and methoxy substituted benzyls, dinitrophenyl (Dnp), t-butyloxymethyl (Bum), benzyloxymethyl (Bom), substituted trityls, 9-phenylfluorenyl, substituted t-butyls, trichloroethyl, nitro benzyl, Troc, phenacyl, 2,2,5,7,8-pentamethylchroman-6-sulfonyl (Pmc), benzydrylamine (BHA), methylbenzydrylamine (Mbha), xanthyl (Xan), 2,4,6-trimethoxybenzyl (Tmob) and other variously substituted analogs, isomers or equivalent groups thereof.

TABLE 1

| Fmoc-Amino Acid Derivative (e) | % Yield | m.p. (°C.) |
|---|---|---|
| 1. Ala | 99[a] | 120-2 |
| 2. Leu | 76 | 75-81 |
| 3. Val | 89 | 74-7 |
| 4. Pro | 74[a] | 62-5 |
| 5. Trp | 80[a] | 136-9 |
| 6. Met | 75 | 92-5 |
| 7. Lys (Boc)[c] | 90 | 75-8 |
| 8. Phe | 79 | 101-3 |
| 9. Glu (tBu) | 84 | 61-5 |
| 10. Ser (tBu) | 78[a] | 90-95 |
| 11. Thr (tBu) | 80[a] | amorphous solid[b] |
| 12. Cys (Trt) | 78[a] | amorphous solid[b] |
| 13. Arg (Mtr) | 86[a] | amorphous solid |
| 14. Ile | 87 | 120-5 |
| 15. Asn (Mbh) | 61 | 193-5 |
| 16. Gln (Mbh) | 91 | 159-65 |
| 17. His (Boc) | 76 | amorphous solid[b] |
| 18. Asp (tBu) | 85 | 85-9 |
| 19. Gly | 83 | 80-90 |
| 20. Tyr (tBu) | 63 | 109-11 |
| 21. Cys (tBu) | 93 | 95-8 |
| 22. Cys (Acm) | 82 | amorphous solid |
| 23. Asn | 75 | amorphous solid |
| 24. Gln | 74 | amorphous solid |

[a]Crude yield
[b]These materials produce "foams" under high vacuum which can be physically broken down to give easily handled, apparently stable powders.
[c]Abbreviations used for side-chain protecting groups (in parentheses) are:
Boc, t-butyloxycarbonyl;
tBu, t-butyl;
Trt, trityl;
Mtr, 4-methoxy-2,3,6-trimethylbenzenesulfonyl;
Mbh, 4,4'-dimethoxybenzhydryl;
Acm, acetamidomethyl.

In the final step (FIG. 1), functionalized $N\alpha$-Fmoc-amino acid esters (e) are coupled directly to solid supports, designated by D-SS, where D is some nucleophilic group, and may be either amino or hydroxyl to yield the compound (f). The coupling to the support is facilitated by the use of a catalyst. The catalyst may be pyridine, 4-dimethylaminopyridine (DMAP), N-methylimidazole, 1-hydroxybenzotriazole (HOBT), or their equivalent. The coupling reaction may be carried out using dimethyformamide (DMF), dimethylacetamide (DMA), N-methylpyrolidone (NMP), methylene chloride, or mixtures of these or their equivalent. The solid supports functionalized by this process may be those based upon materials of current widespread use in peptide synthesis including 1% divinylbenzene (1% DVB)—crosslinked polystyrene, crosslinked polydimethylacrylamide (commercially available Pepsyn and Pepsyn K resins), equivalents thereof containing various degrees of crosslinking and functionalization, functionalized controlled-pore glasses, as well as experimental polymers such as functionalized polyvinylidinedifluoride or polypropylene based membranes, functionalized silicas or aluminas, and ceramic materials, or other insoluble materials onto which a nucleophilic group may be incorporated.

Scheme II

The solid support bound amino acid of formula I can be synthesized using an alternate scheme. In this scheme, a linker is attached to the solid support prior to esterification of the amino acid. The term linker as defined herein is a portion of the compound between the amino acid and the solid support which links the two together. During esterification, the benzylic leaving group undergoes nucleophilic attack by the carboxylate of the amino acid. This esterification also results in the racemization-free attachment of amino acids to solid supports.

In the second scheme, compound II is treated with a hydroxide source to convert X to a hydroxyl group. The resulting compound is then condensed with a solid support, optionally in the presence of a catalyst, to form the solid support linked compound of the formula (IX).

IX

The hydroxyl group of compound IX is then converted to a leaving group such as a halogen or a sulfonyl. The resulting compound undergoes displacement of the leaving group with an N α protected amino acid to yield the compound of formula I or the preferred compound (VIII) as previously described.

Preferably, a halogenated aromatic carboxylic acid analog is reacted with a hydroxide source yielding a hydroxy substituted aromatic carboxylic acid (X).

X

Compound (X) is then condensed to a functionalized support to yield the compound of formula (XI):

XI

The hydroxyl group on compound (XI) is then replaced by a leaving group. In a subsequent step, the leaving group is displaced by an N α protected amino acid to yield the compound of formula VIII.

Figure 2:
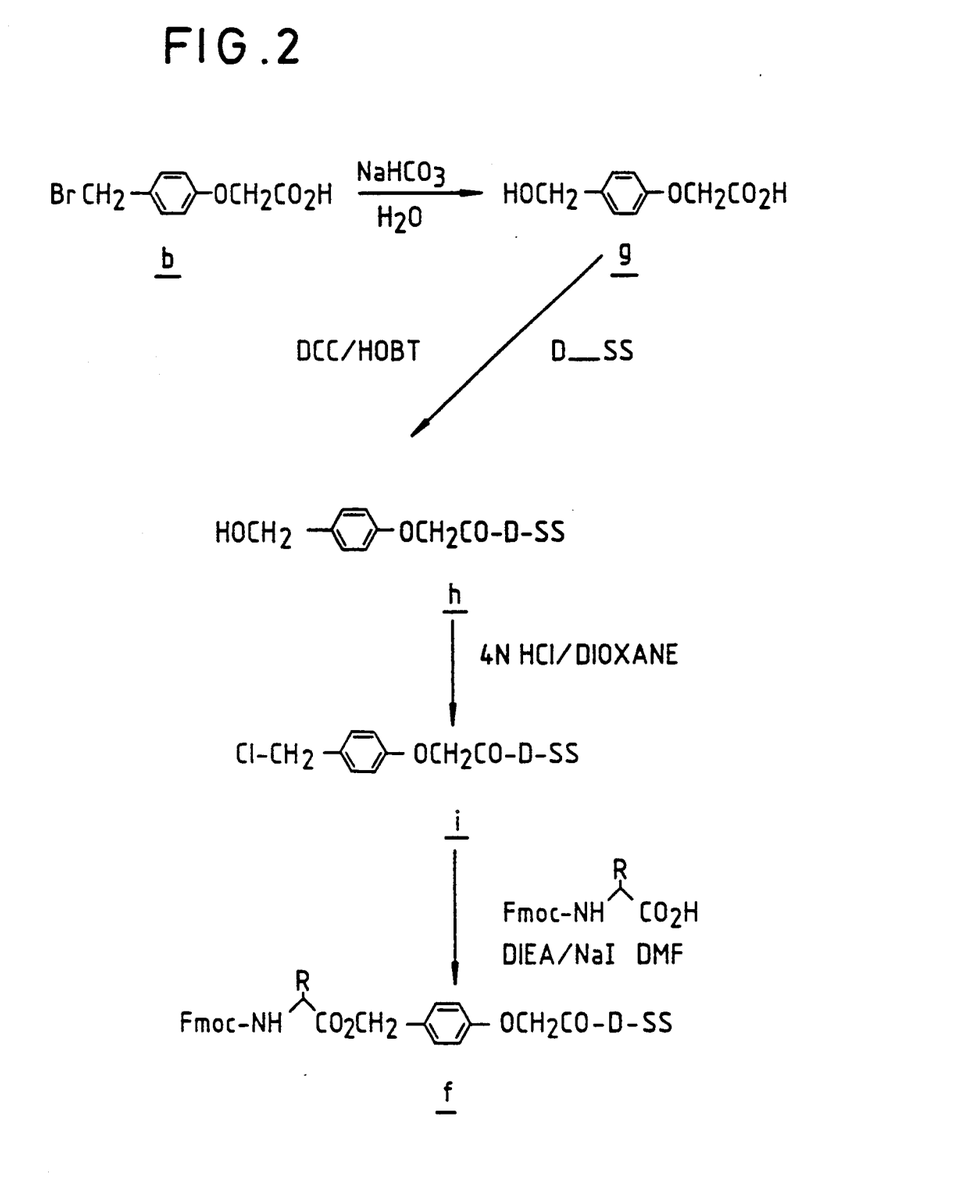
FIG. 2 is an alternate schematic representation for racemization free attachment of C-terminal amino acids to solid supports for peptide synthesis.

In Scheme II, bromo-acid (b) was used as the starting material to facilitate the racemization-free attachment of amino acids to peptide synthesis solid supports as seen in the schematic of FIG. 2.

In the initial step, bromo acid (b) is converted to hydroxy-acid (g) by the action of aqueous NaHCO₃. Other aqueous bases (hydroxide source) buffered to the appropriate pH may be used for this conversion. These include lithium, sodium, potassium, cesium, magnesium, calcium, and barium salts of hydroxide, carbonate, bicarbonate, or their equivalent. In the subsequent step hydroxy-acid (g) is condensed with a solid support containing some nucleophilic functionality, D, which may be hydroxyl or amino. The condensation may be performed using carbodiimides such as dicyclohexyl carbodiimide (DCC) with or without, 1-hydroxybenzotriazole (HOBT) as a catalyst. Other acylation catalysts such as N-hydroxysuccinimide or its equivalent may be used. Active ester derivatives of (g) may also be used for condensation with the solid support to produce functionalized supports (h). Other known modes of carboxyl activation, as previously discussed in relation to the scheme of FIG. 1, may be used to prepare derivatives (h). A key step in this process is the conversion of hydroxymethyl supports (h) to chloromethyl supports (i). This was accomplished by reaction of h with 4N HCl in dioxane at room temperature. Solvents other than dioxane such as ethyl acetate, tetrahydrofuran, acetic acid, methylene chloride, ether, water, or mixtures of these solvents or their equivalent may be used for the chlorination. Other known reagents and methods of replacement of a hydroxyl group by halogen or other leaving group may be employed. Such reagents include $PCl_3$, $PCl_5$, $POCl_3$, triphenylphosphine in $CCl_4$ or $CBr_4$, HBr in an appropriate solvent, $PBr_3$, aryl and alkylsulfonyl chlorides or bromides in solution with an appropriate base such pyridine or diisopropylethylamine (DIEA) or their equivalents. In the final step, the protected amino acid is esterified to the resin by nucleophilic displacement of the leaving group previously incorporated. In this case, the chloromethyl group of (i) was allowed to react at room temperature with an Fmoc-amino acid in dimethylformamide (DMF) containing DIEA and NaI. In the case of Fmoc-alanine, the coupling yield under these conditions was >98% of theoretical and the Fmoc-alanine thus incorporated was quantitatively released by treatment with trifluoroacetic acid. Other known methods for accomplishing esterification via a nucleophilic displacement reaction of a leaving group by a carboxylate, as in the conversion of (i) to (f), may be employed. These have been previously discussed in the description of the chemistry used in Scheme 1. Similarly, other protected amino acids, as previously described in relation to Scheme 1 can be used as starting materials for the esterification.

Racemization Analysis

Figure 3A:
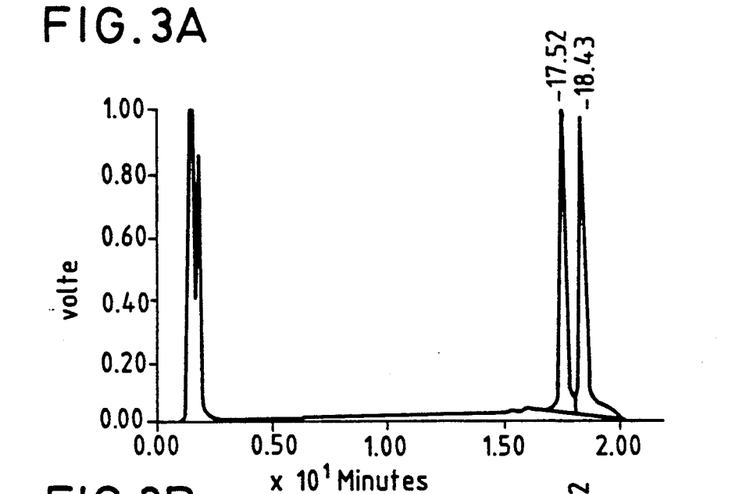
FIG. 3a shows an HPLC chromatogram of GITC derivatives of a standard D,L mixture of phenylalanine.
Figure 3B:
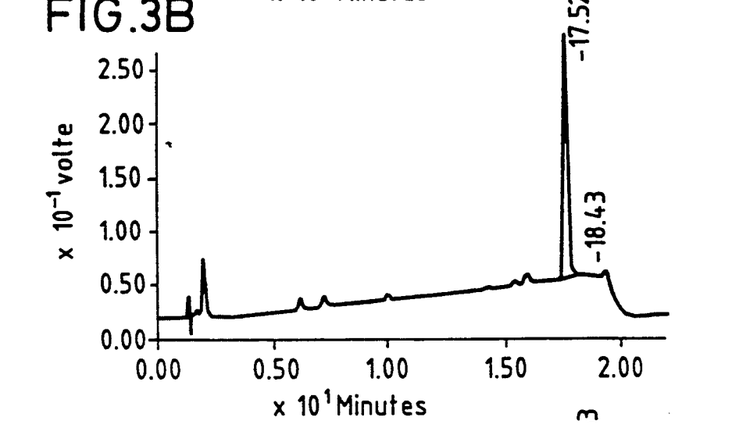
FIG. 3b shows an HPLC chromatogram of GITC derivatives obtained from a resin prepared by the methods of Atherton (*J.C.S. Chem. Comm.*, 336-337 [1981]).
Figure 3C:
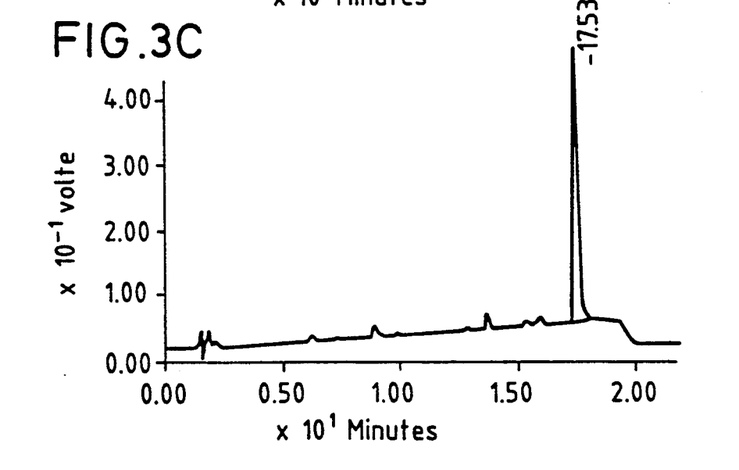
FIG. 3c shows an HPLC chromatogram of GITC derivative obtained from a resin prepared by the methods of this invention.
Figure 4A:
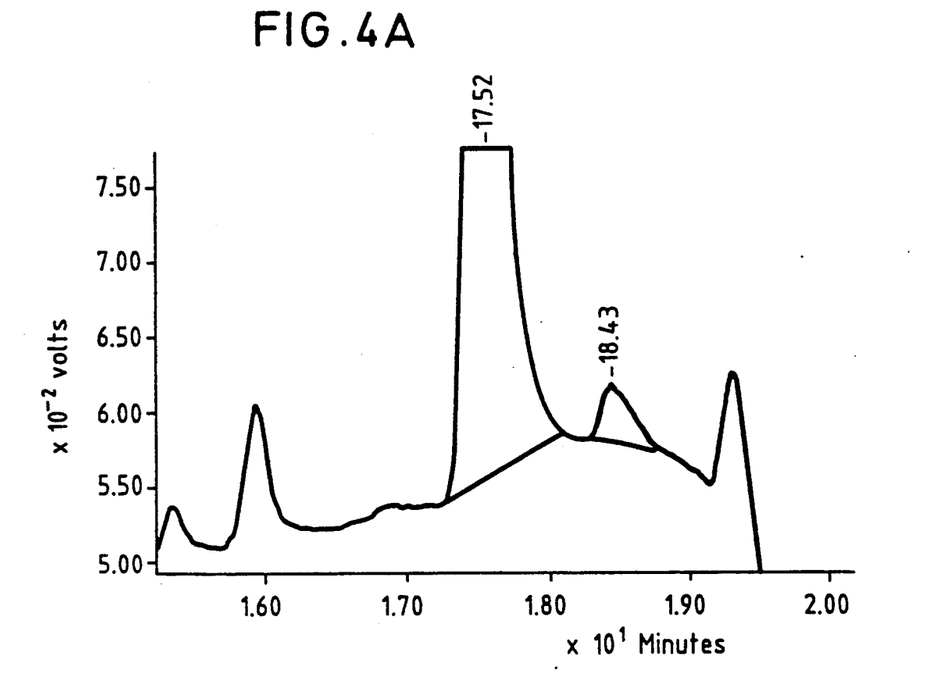
FIG. 4a shows the HPLC chromatogram of FIG. 3b as expanded by computer.
Figure 4B:
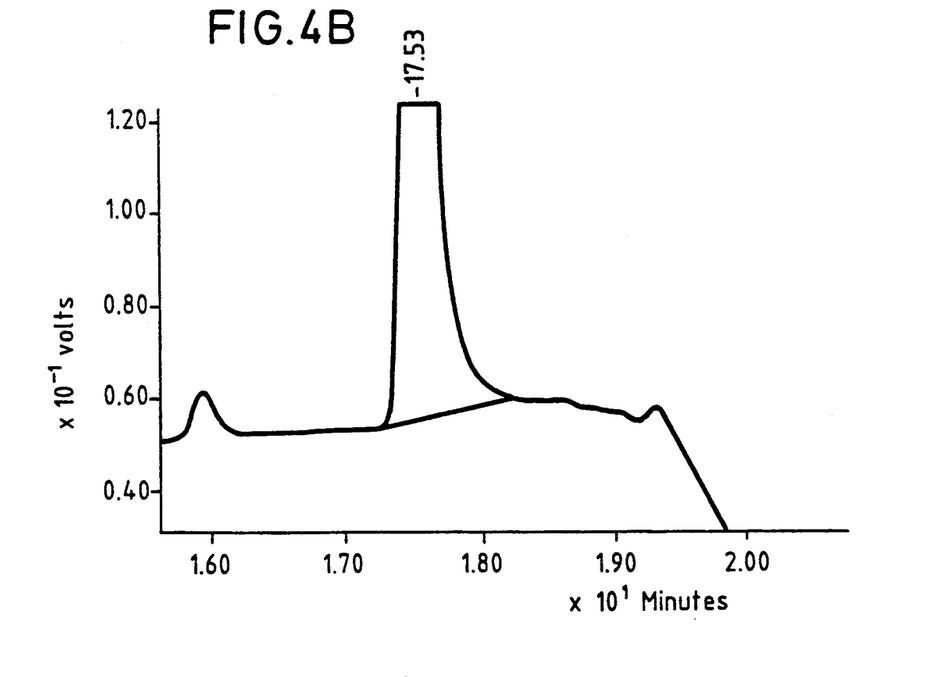
FIG. 4b shows the HPLC chromatogram of FIG. 3c as expanded by computer.
Figure 5A:
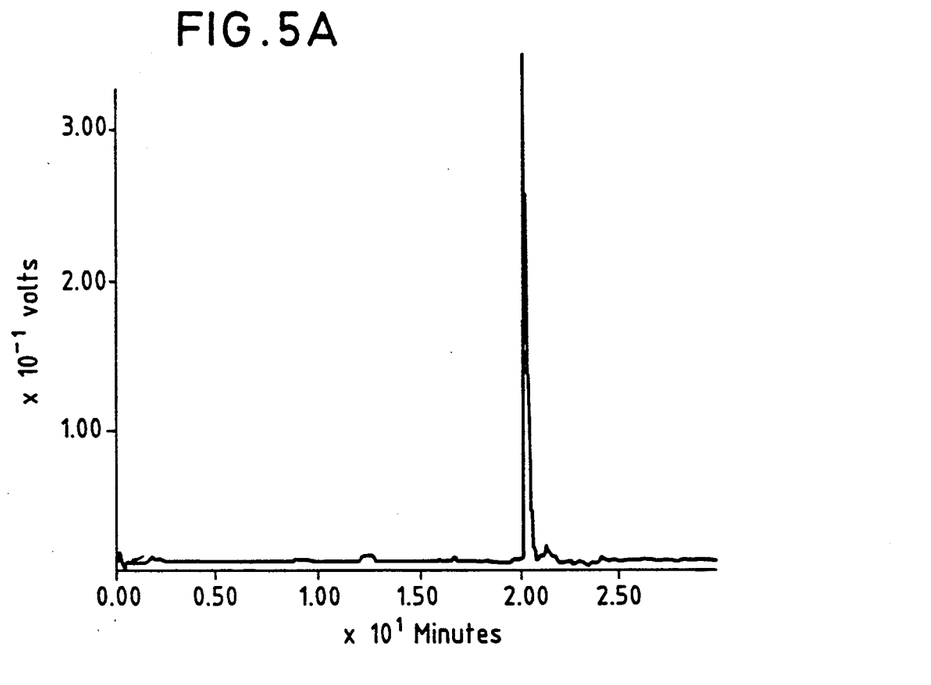
FIG. 5a shows an HPLC chromatogram for peptide Ala-Asn-Lys-Gly-Phe-Leu-Glu-Glu-Val prepared starting with Fmoc-Val-linker-Pepsyn K resin prepared by methods of this invention.
Figure 5B:
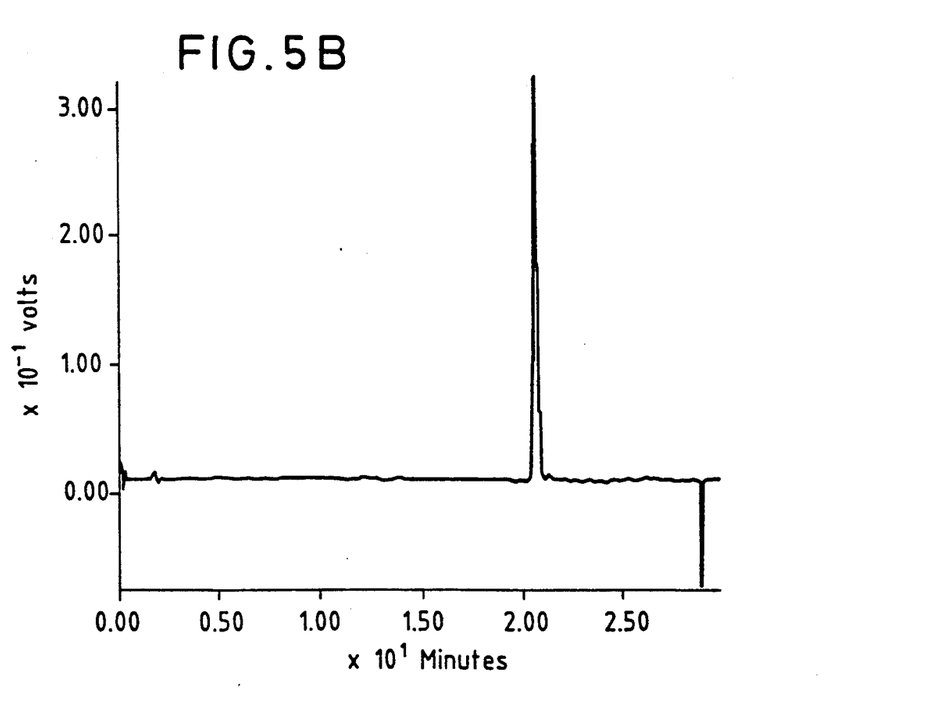
FIG. 5b show the same peptide as shown in 5a prepared starting with Fmoc-Val-linker-Pepsyn K resin using the linker of Sheppard, R. C. and Williams, B. J., *Int. J. Particles Protein Res.* 20:451–454 [1982] and carboxyl group activation method of Atherton E. et al., *J.C.S. Chem. Commun.* 336–337 [1981].

In order to demonstrate the optical purity of the solid support bound amino acids prepared by the processes described herein, a chiral derivatizing agent, 2,3,4,6-tetra-O-acetyl-β-D-glucopyranosyl isothiocyanate (GITC), (Nimura, N. et al. *Journal of Chromatography* 202:375-9 [1980]; Kinoshita, T. et al. *Journal of Chromatography* 210:77-81 [1981]) which is capable of converting D,L amino acid mixtures into mixtures of reverse phase HPLC resolvable diastereomers, was used. In these experiments Pepsyn-K based resins prepared by the new processes described herein were compared with commercially available resins prepared by current art methods (Atherton, E. et al., *J.C.S. Chem. Commun.* 336-337 [1981]) and commercially available D,L-amino acid standard mixtures (Sigma Chemical Co., St. Louis, Mo.). After removal of the Fmoc group from the Fmoc-amino acid-Pepsyn K resins with 20% piperidine in DMF (v/v), followed by washout of excess reagent with DMF then CH$_2$Cl$_2$, the free amino acids were cleaved from the resins with neat trifluoroacetic acid (TFA). The TFA was separated from the resins and evaporated to dryness to give the free amino acids as dry TFA salts. The free amino acids were derivatized with GITC reagent as described in the literature (Nimura, N. et al., *Journal of Chromatography* 202:375–9 [1980]; Kinoshita, T. et al., *Journal of Chromatography* 210:77–81 [1981]). The results of the HPLC analysis (C-18 column, 15-minute linear gradient of 20 to 40% acetonitrile in water containing 0.1% TFA) of the amino acids obtained in this manner from Fmoc-Phe-Pepsyn K resins, prepared by the methods of this invention and commercial Fmoc-Phe-Pepsyn K product (Atherton, E. et al., *J.C.S. Chem. Commun.* 336–337 [1981]) are shown in FIGS. 3 and 4. The phenylalanine derivative obtained from the resin prepared by the methods of this invention was essentially free of D-isomer contaminant and is therefore consistent with lack of racemization. In contrast, the commercial phenylalanine derivative was found to contain a substantial amount (2%) of D-isomer contaminant as quantitated by peak integration. FIG. 3b shows a small peak eluting at 18.43 minutes which corresponds to 2% contamination by D-isomer in the commercial product produced by the methods of Atherton et al.

Peptide Synthesis

The solid support bound amino acids of Formula I are used for the synthesis of specific peptide sequences. The solid support is chemically functionalized to anchor the first peptide building block. The synthesis of the specific peptide sequence is performed either manually or by automated synthesis. Standard chemical protocols for the stepwise construction of peptides can be employed. Examples of such methods are Gutte, B. & Merrifield, R. B. (1971) *J. Biol. Chem.* 246:1922–1941; Kent, S. B., et al., (1978) *Anal. Chem.* 50:155–159; Wong, T. W. & Merrifield, R. B. (1980) *Biochemistry* 19:3233–3238; Arshady, R., et al., (1981) *J. Chem. Soc. Perkin Trans. I*, 529–537; Atherton, E., et al., (1981) *J. Chem. Soc., Perkin Trans. I*, 538–546; Stewart, J. M. & Young, J. D. (1984) in *Solid Phase Peptide Synthesis*, 2nd edn., Pierce Chemical Co., Rockford, Ill.; and Atherton, E., Sheppard, R. C. & Ward, P. (1985) *J. Chem. Soc., Perkin Trans. I*, 2065–2073. After the assembly of the desired specific sequence, the protecting groups can be removed to generate biologically functional molecules.

Depending on the linkage to the solid support, the synthesized peptide can either be cleaved off for subsequent characterization and/or identification or it can be left on the solid support in an unprotected form.

The present invention will now be illustrated by the following examples which are not to be considered limiting in any way.

EXAMPLE 1

Preparation of 4-Bromomethylphenoxyacetic acid (b)

To 4-methylphenoxyacetic acid (87.3 g, 0.525 mole) and N-bromosuccinimide (112.2 g. 0.63 mole) was added 900 ml of dry CHCl$_3$ and 100 mg benzoyl peroxide and the mixture was refluxed for 2.5 hours. The mixture was allowed to cool and was stored overnight at 4°. The crystals which had formed were collected by vacuum filtration and were washed twice with 50 ml of ice-cold CHCl$_3$ followed by 50 ml washes with water. After drying in vacuo over P$_2$O$_5$ to a constant weight, 52.9 g of white product (mp 122°–4° C.) were obtained. To obtain additional product, the organic mother liquor was washed with water (3×150 ml), and 150 ml brine. After drying over Na$_2$SO$_4$ and filtration, the solvent was removed in vacuo and the residue crystallized from 90 ml boiling CHCl$_3$. The crystals were collected by vacuum filtration, washed three times with 20 ml of CHCl$_3$/hexanes (1:1) and dried in vacuo to give 17.6 g of additional product (mp 121°–2° C.). Total yield, 70.5 g (55%). The product displayed an $R_f$=0.33 upon TLC (silica gel 60) developed with 95:5 CHCl$_3$:acetic acid.
$^1$H NMR (300 MHz, CDCl$_3$, ppm δ relative to tetramethylsilane):4.41 (s,2H), 4.62 (s, 2H), 6.24 (broad s, 1H), 6.82 (d, J=8.7 Hz, 2H), 7.28 (d, J-8.7 Hz, 2H).

EXAMPLE 2

Preparation of 2,4-Dichlorophenyl-4-bromomethylphenoxy acetate (c)

To 4-bromomethylphenoxyacetic acid (20 g, 81.6 mole) and 2,4-dichlorophenol (14 g, 85.7 mole) suspended in 100 ml ethyl acetate at 0° C. was added solid dicyclohexylcarbodiimide (17.7 g, 85.8 mole) in portions with stirring. After two hours at 0° C., 200 ml of ethyl acetate was added to the thick suspension that resulted, and stirring was allowed to proceed for 30 minutes as the mixture was allowed to warm to room temperature. Insoluble dicyclohexylurea was removed by filtration and was washed with ethyl acetate (3×30 ml). The combined filtrate and washes were concentrated in vacuo and the residue was dissolved in 35 ml boiling ethyl acetate. Upon cooling to room temperature, crystalline product had formed. After addition of 155 ml hexanes in portions with mixing, the product was collected by vacuum filtration, washed with hexanes/ethyl acetate (9:1), and dried in vacuo to yield 26.8 g (85%) of crystalline product (mp 114°–6° C.). The product was homogeneous by TLC (silica gel 60) and had an $R_f$=0.50 when developed with hexanes:ethyl acetate (8:2).

$^1$H NMR (300 MHz, CDCl$_3$, ppm δ relative to tetramethylsilane): 4.51(s, 2H), 4.98(s,2H), 6.97(d, J=10.2 Hz, 2H), 7.12(d, J=10.2 Hz, 1H). 7.28–7.4(m, 3H, includes d, J=10.2 Hz, 2H), 7.48(d, J=3.4 Hz, 1H).

EXAMPLE 3

Preparation of 2,4-Dichlorophenyl-4-iodomethyl phenoxyacetate (d)

To 2,4-dichlorophenyl-4-bromomethyl phenoxyacetate (7.21 g, 18.48 mmole) was added to a solution of anhydrous sodium iodide (2.96 g, 19.7 mmole) in 100 ml acetone. The mixture was stirred for 30 minutes at room temperature. The insoluble sodium bromide which formed was removed by vacuum filtration and washed three times with 5 ml portions of acetone. Removal of the solvent in vacuo from the combined filtrate and washes furnished 8.1 g (100%) of a slightly yellow crystalline solid (mp 121°–2° C.) which was used for synthesis without further purification. The product exhibited $R_f$=0.59 on TLC (silica gel 60) developed with hexanes:ethyl acetate (1:1).

EXAMPLE 4

Preparation of Amino Acid Derivative (e)

To 4-iodomethyl active ester (d) (1.0 g, 2.3 mmole) and the appropriate Nα-Fmoc-amino acid (2.5 mmole) dissolved or suspended in 4 to 5 ml dimethylacetamide- :acetone (1:1) was added diisopropylethylamine (0.45 ml, 2.6 mmole) dropwise with stirring at room temperature. In general, a solution results within one hour and reactions are complete within two hours as judged by disappearance of d on TLC. To the reaction mixture was added 20 ml ether:ethyl acetate (1:1) and the organic phase was washed in succession with 10 ml portions of water, 5% aqueous sodium bicarbonate, 5% aqueous sodium thiosulfate, water, brine and dried with anhydrous MgSO4. After filtration to remove drying agent, the products were obtained by removal of solvent and drying in vacuo. When possible, the products were crystallized from an appropriate solvent or solvent pair. In the case of the Cys(Acm) Asn, and Gln derivatives, the reactions were carried out similarly starting with the 4-bromomethyl active ester c and were conducted using neat dimethylformamide as solvent. In the case of the Asn and Gln derivatives, the products precipitated from the organic phase during the usual aqueous washes. These products were collected by filtration, washed with ether followed by several portions of water and dried in vacuo over $P_2O_5$.

EXAMPLE 5

Preparation of Solid Supports Derivatized with Protected Amino Acids via a Functional Linking Group (f)

Commercial Pepsyn K TM (250 umole sarcosine methyl ester/g) resin (25 g) was treated overnight at room temperature with 60 ml ethylenediamine. The ethylenediamine was removed by filtration and the resin was washed successively six times with dimethylformamide (DMF), six times with $CH_2Cl_2$, three times with ether and dried in vacuo. In order to determine the resulting amine substitution level, a small portion of the ethylenediamine derivatized resin was treated with a large excess of Fmoc-alanine pentafluorophenyl ester (0.3M in DMF) in the presence of one equivalent of 1-hydroxybenzotriazole. After one hour at room temperature, the amino groups incorporated on the resin were completely coupled to Fmoc-alanine as evidenced by failure of the resin to react with ninhydrin reagent. The resin was washed successively six times each with DMF, $CH_2Cl_2$, ether and dried in vacuo. The Fmoc-group incorporation was quantitated spectrophotometrically after cleavage with piperidine in $CH_2Cl_2$. Correction for the weight gain of the incorporated Fmoc-alanine indicated that the starting ethylenediamine derivatized Pepsyn K TM had a substitution of 0.24 mmole amino groups/g. This amino-Pepsyn K derivative was used to obtain the results reported in Table 2.

In a typical solid-support derivatization experiment, 0.5 to 1.5 g of the ethylenediamine derivatized Pepsyn K resin was used. The appropriate Fmoc-amino acid derivative (e) was dissolved in an amount of DMF just sufficient to completely swell and wet the resin (about 2.5 ml/g resin) and was added to the resin together with 4-dimethylaminopyridine (exact amounts of reagents are given in Table 2). After gentle mixing to remove any entrained air bubbles, the mixture was allowed to stand at room temperature for three hours. In general a three-hour reaction time was sufficient to completely, or nearly completely, couple all the resin-bound amino groups as indicated by lack of reaction of the resin products with ninhydrin reagent. After the coupling reaction the resins were washed successively as described above for the work-up of the starting ethylenediame derivatized Pepsyn K. After drying in vacuo to constant weight, samples of the resins were subjected to spectrophotometric analysis of the Fmoc-chromophore released upon treatment with piperidine in $CH_2Cl_2$. The results obtained are given in Table 2.

TABLE 2

Solid Supports (f) Prepared by Coupling of Amino Acid Derivatives (e) to Amino-Pepsyn-KA, 0.24 mmole-$NH_2$/g

| Starting Fmoc-Amino Acid Derivative (e) (equivalents) | Catalyst Equivalents | Final Substitution[b] (mmole Fmoc/g) |
|---|---|---|
| Val (3.0) | 0.7 (DMAP)[a] | 0.184 |
| Phe (3.0) | 0.7 (DMAP) | 0.196 |
| Trp (3.0) | 0.7 (DMAP) | 0.175 |
| Ala (3.0) | 0.7 (DMAP) | 0.187 |
| Ile (2.0) | 0.7 (DMAP) | 0.171 |
| Glu (2.0) | 0.7 (DMAP) | 0.166 |
| Gln (Mbh)[a] (2.5) | 0.7 (DMAP) | 0.170 |
| Arg (Mtr) (2.5) | 0.7 (DMAP) | 0.181 |
| His (Boc) (2.5) | 0.7 (DMAP) | 0.160 |
| Met (2.5) | 0.7 (DMAP) | 0.166 |
| Cys (Trt) (3.0) | 2.6 (DMAP) | 0.150[c] |
| Lys (Boc) (2.5) | 2.2 (DMAP) | 0.191 |
| Ser (tBu) (2.5) | 2.2 (DMAP) | 0.177 |
| Thr (tBu) (2.5) | 2.2 (DMAP) | 0.171 |
| Asn (Mbh) (2.5) | 2.2 (DMAP) | 0.190 |
| Pro (2.5) | 0.7 (DMAP) | 0.213 |
| Asp (tBu) (2.5) | 0.7 (DMAP) | 0.178 |
| Gly (2.5) | 0.7 (DMAP) | 0.186 |
| Try (tBu) (2.5) | 0.7 (DMAP) | 0.190 |
| Leu (2.0) | 0.75 (DMAP) | 0.195 |
| Cys (Acm) (2.5) | 0.7 (DMAP) | 0.184 |

[a]DMAP is an abbreviation for 4-dimethylaminopyridine. Side chain protecting group abbreviations are the same as given in Table 1.
[b]Coupling time is 3 hours.
[c]A substitution level of 0.19 mmole Fmoc/g was achieved when 2.5 equivalents of Fmoc-Cys (Trt) derivative was used and 3.0 equivalents of pyridine substituted for DMAP.

EXAMPLE 7

Analysis for Racemization-Free Attachment

Fmoc-amino acid derivatized Pepsyn K TM resins (100 mg) (MilliGen) were placed in 16×100 mm glass test tubes. The resins were washed with 10 ml $CH_2Cl_2$ and 10 ml dimethylformamide. The washes were discarded after careful decantation from the settled resins. The Fmoc-protecting group was removed by reaction of the resins with 5 ml 20% piperidine in dimethylformamide (v/v) for 10 minutes. The resins were washed with DMF (3×10 ml) and $CH_2Cl_2$ (6×10 ml). Amino acids were cleaved from the resins by treatment with 5 ml neat trifluoroacetic acid for 20 minutes. The trifluoroacetic acid solutions of amino acids thus cleaved were evaporated by a stream of dry nitrogen and dried further in vacuo over solid KOH. The residues thus obtained were dissolved in 0.4 ml 50% aqueous acetonitrile (v/v) containing 0.4% triethylamine. The amino acid solutions (0.05 ml) were added to 0.10 ml of GITC solution [0.2% GITC (w/v) in acetonitrile]. After a minimum of 30 minutes reaction, aliquots (2 microliters) of GITC derivatives were subjected to HPLC analysis. The GITC derivatives thus prepared were stable in this solution for up to about 12 hours at room temperature. D,L amino acid standards were derivatized with GITC solution as described above starting with a 5 mg/ml solution of standard in 50% aqueous acetonitrile (v/v) containing 0.4% triethylamine. Injection volumes were 5 microliters.

HPLC analysis was performed using a Waters 600 gradient HPLC system with a Waters Lambda-Max Model 481 detector set at 220 nm, 1 AUFS. The column was a Waters Delta Pak TM C-18-300 A, 3.9 mm×15 cm. Binary gradient elution buffers were: (a) 0.1% trifluoroacetic acid in water; and (b) 0.07% trifluoroacetic acid in acetonitrile.

A linear gradient of 20 to 40% buffer B at a flow rate of 1 ml/minute over 15 minutes was used. This was followed by an additional minute at 40% buffer B. The column was then allowed to reequilibrate by pumping 20% buffer B for at least 6 minutes before injection of the next sample.

EXAMPLE 8

Preparation of 4-hydroxymethylphenoxyacetic acid (g) from 4-bromomethylphenoxyacetic acid (b)

To 4-bromomethylphenoxyacetic acid (2.50 g, 10.2 mmole) was slowly added approximately 70 ml 5% aqueous $NaHCO_3$ with effervescence. The resulting cloudy solution was stirred for two hours at room temperature. After filtration the solution was cooled in an ice bath and carefully acidified to pH 2 with 6M HCl. The product was extracted with ethyl acetate (3×50 ml). The combined organic phase was washed with brine, dried over $MgSO_4$, filtered, and the solvent was removed by rotary evaporation. After drying in vacuo, 1.53 g (82.5%) of crude white product was obtained. After recrystallization from a mixture of ethyl acetate (10 ml) and hexanes (10 ml), 1.23 g (66%) of purified white crystalline product was obtained. mp. 112°–115° C. (114°–116° C. reported by Sheppard, R. C. and Williams, B. J., *Int. J. Peptide Protein Res.* 20:451–454 [1982])

EXAMPLE 9

Preparation of 4-chloromethyl-Pepsyn KA TM resin derivative (i) and conversion to peptide synthesis support (f)

To 200 mg Pepsyn KA TM resin (MilliGen) (0.2 mmole hydroxymethyl groups/g) was added 1 ml of 4N HCl in dioxane. After two hours at room temperature the resin was washed thoroughly by decantation of added dimethylformamide (95×4 ml). To the resulting slurry of dimethylformamide wetted resin were added Fmoc-alanine (100 mg, 0.32 mmole), diisopropylethylamine (0.061 ml, 0.35 mmole), anhydrous sodium iodide (40 mg, 0.27 mmole), and the mixture was gently mixed by periodic manual shaking. The mixture was allowed to react for 20 hours at room temperature after which the resin was washed: 3×4 ml dimethylformamide, 3×4 ml water, 3×4 ml methanol, and 3×4 ml ether. The resin was dried in vacuo and analyzed for Fmoc-substitution. The resin product was found to contain 0.186 mmole Fmoc-alanine/g (98.4% of theoretical). Treatment of a portion of the product with neat trifluoroacetic acid for 1.5 hours at room temperature followed by analysis of Fmoc-substitution indicated that the Fmoc-alanine thus incorporated was quantitatively cleaved.

EXAMPLE 10

Peptide Synthesis

In order to demonstrate the peptide synthesis utility of the resins (Table 2) prepared by the methods of this invention, a 9-residue peptide (Ala-Asn-Lys-Gly-Phe-Leu-Glu-Glu-Val) was synthesized starting with the Fmoc-Val-linker-Pepsyn K resin prepared as previously described. As a control for comparison, the same peptide was synthesized starting with commercially available Fmoc-Val-linker-Pepsyn K resin (Cambridge Research Biochemicals Ltd., Cambridge, England) prepared by prior art methods. (Atherton, E. et al., *J.C.S. Chem. Commun.* 336–337 [1981]). Both syntheses were performed on the MilliGen/Biosearch Model 9050 continuous flow automated peptide synthesizer using commercially available (MilliGen/Biosearch, Burlington, Mass.) Fmoc-amino acid-pentafluorophenyl esters as preactivated monomers and standard (default) protocols specified by MilliGen/ Biosearch Express TM peptide synthesis software (Version 1.2). Both syntheses were performed simultaneously on the same instrument using two separate column reactors such that the same reagents or solvents were simultaneously used in both syntheses. Both peptides were deprotected and isolated. Both syntheses produced the target peptide in >80% crude yield and with comparable high purities as evidenced by high performance liquid chromatography (HPLC) chromatograms (FIG. 3). FIG. 3a shows a chromatogram for the 9-residue peptide prepared using the solid support bound amino acid of this invention. FIG. 3b show a chromatogram for a similar 9-residue peptide prepared using a commercially available solid support bound amino acid resin. Separations were performed using a Delta-Pak TM C-18 column (100 A pore, 5um, 0.39×15 cm) and a flow rate of 1.0 ml/minute. Products were detected by absorbance at 220 nm. Gradient elution: (Eluent A, 0.1% (v/v) trifluoracetic acid in water; Eluent B, 0.1% (v/v) trifluoroacetic acid in 95% acetonitrile containing 5% water) 6% to 62% B in 30 minutes linearly. The identity of both products was established by amino acid analysis and mass spectral data. (M+ =1005±2, 1006 calculated)

EQUIVALENTS

Those skilled in the art will recognize, or be able to ascertain, using no more than routine experimentation, many equivalents to the specific embodiments of the invention described herein. These and all other equivalents are intended to be encompassed by the following claims.

I claim:

1. An enantiomerically pure compound of the formula:

wherein

Z is an $N\alpha$ amino acid protecting group;

B is a naturally occurring D or L amino acid having protected or unprotected side chains;

$R_1$ and $R_2$ are the same or different and are selected from the group consisting of hydrogen, linear or branched, saturated or unsaturated alkyl of 1 to 6 carbon atoms and phenyl;

A is a substituted or unsubstituted phenyl ring wherein the substituents are selected from the group consisting of alkyl of 1 to 6 carbon atoms, halo, nitro, alkoxy of 1 to 6 carbon atoms and combinations thereof;

Y is a hydrocarbon chain having a linear or branched, saturated or unsaturated alkyl of 1 to 6 carbon atoms, phenyl or phenalkyl having an alkyl group of 1 to 6 carbon atoms; and p1 m is zero or one.

2. A compound of claim 1 wherein the Nα protecting group and amino acid side chain protecting group is selected from the group consisting of 9-fluorenyl-methloxycarbonyl, t-butyloxycarbonyl, t-butyl, trityl, thio-t-butyl, 4-methoxy-2,3,6-trimethylbenzenesulfonyl, 4,4'-dimethoxybenzhydryl, acetamidomethyl, dithiosuccinyl, carbobenzyloxycarbonyl, 2-nitropyridinesulfenyl, trifluoroacetyl, 2(p-biphenylisopropyloxycarbonyl), 4-methoxybenzyloxycarbonyl, tosyl, 9-phenylfluorenyl, 2-nitrophenylsulfenyl, benzyl, p-nitrocarbobenzyloxycarbonyl, t-amyloxycarbonyl, 2,2-[bis(4-nitrophenyl)]-ethyloxycarbonyl, adamantyloxycarbonyl, 2,2,2-trichloroethyloxycarbonyl, dinitrophenyl, t-butyloxymethyl, benzyloxymethyl, trichloroethyl, nitrobenzyl, phenacyl, 2,2,5,7,8-pentamethylchroman-6-sulfonyl, benzydrylamine, methylbenzydrylamine, xanthyl and 2,4,6-trimethoxybenzyl.

3. An enantiometically pure compound having the formula:

wherein

Z is an Nα amino acid protecting group;

B is a naturally occurring D or L amino acid having protected or unprotected side chains; and m is zero or one and n is an integer from zero to 12.

4. A compound of claim 3 wherein the Nα protecting group and amino acid side chain protecting group is selected from the group consisting of 9-fluorenylmethyloxycarbonyl, t-butyloxycarbonyl, t-butyl, trityl, thio-t-butyl, 4-methoxy-2,3,6-trimethylbenzenesulfonyl, 4,4'-dimethoxybenzhydryl, acetamidomethyl, dithiosuccinyl, carbobenzyloxycarbonyl, 2-nitropyridinesulfenyl, trifluoroacetyl, 2(p-biphenylisopropyloxycarbonyl), 4-methoxybenzyloxycarbonyl, tosyl, 9-phenylfluorenyl, 2-nitrophenylsulfenyl, benzyl, p-nitrocarbobenzyloxycarbonyl, t-amyloxycarbonyl, 2,2-[bis(4-nitrophenyl)]-ethyloxycarbonyl, adamantyloxycarbonyl, 2,2,2-trichloroethyloxycarbonyl, dinitrophenyl, t-butyloxymethyl, benzyloxymethyl, trichloroethyl, nitrobenzyl, phenacyl, 2,2,5,7,8-pentamethylchroman-6-sulfonyl, benzydrylamine, methylbenzydrylamine, xanthyl and 2,4,6-trimethoxybenzyl.

5. A compound of claim 3, wherein Z is 9-fluorenylmethyloxycarbonyl, m=1 and n=1.

6. An enantiomerically pure compound of the formula:

wherein

Z is an Nα amino acid protecting group; B is a naturally occurring D or L amino acid having protected or unprotected side chains;

$R_1$ and $R_2$ are independently selected from the group consisting of hydrogen, linear or branched, saturated or unsaturated alkyl of 1 to 6 carbon atoms and phenyl;

A is a substituted or unsubstituted phenyl ring wherein the substituents are selected from the group consisting of alkyl of 1 to 6 carbon atoms, halo, nitro, alkoxy or 1 to 6 carbon atoms and combinations thereof;

m is zero or 1; and n is 1 to twelve.

7. A compound of claim 6 wherein the Nα protecting group and amino acid side chain protecting group is selected from the group consisting of 9-fluorenylmethoxycarbonyl, t-butyloxycarbonyl, t-butyl, trityl, thio-t-butyl, 4-methoxy-2,3,6-trimethylbenzenesulfonyl, 4,4'-dimethoxybenzhydryl, acetamidomethyl, dithiosuccinyl, carbobenzyloxycarbonyl, 2-nitropyridinesulfenyl, trifluoroacetyl, 2(p-biphenylisopropyloxycarbonyl), 4-methoxybenzyloxycarbonyl, tosyl, 9-phenylfluorenyl, 2-nitrophenylsulfenyl, benzyl, p-nitrocarbobenzyloxycarbonyl, t-amyloxycarbonyl, 2,2-[bis(4-nitrophenyl)]-ethyloxycarbonyl, adamantyloxycarbonyl, 2,2,2-trichloroethyloxycarbonyl, dinitrophenyl, t-butyloxymethyl, benzyloxymethyl, trichloroethyl, nitrobenzyl, phenacyl, 2,2,5,7,8-pentamethylchroman-6-sulfonyl, benzydrylamine, methylbenzydrylamine, xanthyl and 2,4,6-trimethoxybenzyl.

* * * * *

UNITED STATES PATENT AND TRADEMARK OFFICE
CERTIFICATE OF CORRECTION

PATENT NO.   : 5,187,270

DATED        : February 16, 1993

INVENTOR(S)  : Michael S. Bernatowicz

It is certified that error appears in the above-identified patent and that said Letters Patent is hereby corrected as shown below:

In Claim 1, Column 16, Line 68, before "m is zero or one" delete "p1".

Signed and Sealed this

Twenty-eighth Day of December, 1993

Attest:

BRUCE LEHMAN

*Attesting Officer*       Commissioner of Patents and Trademarks